(12) United States Patent
Sims

(10) Patent No.: US 8,454,562 B1
(45) Date of Patent: Jun. 4, 2013

(54) INFUSION PUMP SYSTEM AND METHOD

(75) Inventor: Geoffrey C. Sims, Campbell, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 0 days.

(21) Appl. No.: 13/553,921

(22) Filed: Jul. 20, 2012

(51) Int. Cl.
*A61M 37/00* (2006.01)
*A61M 5/178* (2006.01)
*A61M 5/315* (2006.01)

(52) U.S. Cl.
USPC ............... 604/151; 604/167.06; 604/221

(58) Field of Classification Search
USPC .......... 604/131–133, 141, 151–152, 154, 604/156–158, 167.06, 221
See application file for complete search history.

(56) References Cited

U.S. PATENT DOCUMENTS

| | | |
|---|---|---|
| 4,373,527 A | 2/1983 | Fischell |
| 4,652,260 A | 3/1987 | Fenton et al. |
| 4,668,220 A | 5/1987 | Hawrylenko |
| 4,902,278 A | 2/1990 | Maget et al. |
| 5,176,632 A | 1/1993 | Bernardi |
| 5,672,167 A | 9/1997 | Athayde et al. |
| 5,718,562 A | 2/1998 | Lawless |
| 5,800,420 A | 9/1998 | Gross et al. |
| 6,127,061 A | 10/2000 | Shun et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,491,684 B1 | 12/2002 | Joshi et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Accu-Chek Spirit, "Pump Therapy Made for You," Roche, 2006, 6 pages.

(Continued)

*Primary Examiner* — Quynh-Nhu H Vu
(74) *Attorney, Agent, or Firm* — Fish & Richardson P.C.

(57) ABSTRACT

Some embodiments of an infusion pump system may be configured to provide air pressure equilibrium between the ambient air pressure external to the infusion pump system and the internal air pressure inside the infusion pump system. In particular embodiments, the infusion pump system can be equipped with an air-transmissible, liquid-tight seal along an interface between a pump body and a cap device configured to attach to the pump body.

20 Claims, 9 Drawing Sheets

U.S. PATENT DOCUMENTS

| | | |
|---|---|---|
| 6,537,268 B1 | 3/2003 | Gibson et al. |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 669,668 A1 | 12/2003 | Kleeman et al. |
| 6,656,158 B2 | 12/2003 | Gregory et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 * | 12/2003 | Møller .......................... 604/211 |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,957 B2 * | 9/2004 | Carpenter et al. ......... 604/93.01 |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,232,423 B2 | 6/2007 | Mernoe |
| 7,597,682 B2 * | 10/2009 | Moberg ..................... 604/131 |
| 7,654,982 B2 * | 2/2010 | Carlisle et al. ................ 604/132 |
| 7,875,022 B2 * | 1/2011 | Wenger et al. ............ 604/890.1 |
| 2001/0041869 A1 | 11/2001 | Causey, III et al. |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0016568 A1 | 2/2002 | Lebel |
| 2002/0032402 A1 | 3/2002 | Daoud et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0156462 A1 | 10/2002 | Stultz |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0161744 A1 | 8/2003 | Vilks et al. |
| 2003/0199825 A1 | 10/2003 | Flaherty |
| 2003/0216683 A1 | 11/2003 | Shekalim |
| 2003/0216686 A1 | 11/2003 | Lynch et al. |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0187952 A1 | 9/2004 | Jones |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0038332 A1 | 2/2005 | Saidara et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0113745 A1 | 5/2005 | Stultz |
| 2005/0124866 A1 | 6/2005 | Elaz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |

| | | | |
|---|---|---|---|
| 2005/0273059 A1 | 12/2005 | Mernoe et al. | |
| 2006/0041229 A1 | 2/2006 | Garibotto et al. | |
| 2006/0069382 A1 | 3/2006 | Pedersen | |
| 2006/0074381 A1 | 4/2006 | Malave et al. | |
| 2006/0095014 A1 | 5/2006 | Ethelfeld | |
| 2006/0135913 A1 | 6/2006 | Ethelfeld | |
| 2006/0142698 A1 | 6/2006 | Ethelfeld | |
| 2006/0151545 A1 | 7/2006 | Imhof et al. | |
| 2006/0178633 A1 | 8/2006 | Garibotto et al. | |
| 2006/0184119 A1 | 8/2006 | Remde et al. | |
| 2006/0200073 A1 | 9/2006 | Radmer et al. | |
| 2006/0206054 A1 | 9/2006 | Shekalim | |
| 2006/0247581 A1 | 11/2006 | Pedersen et al. | |
| 2007/0073228 A1 | 3/2007 | Mernoe et al. | |
| 2007/0073236 A1 | 3/2007 | Mernoe et al. | |
| 2007/0088271 A1 | 4/2007 | Richards | |
| 2007/0093750 A1 | 4/2007 | Jan et al. | |
| 2007/0106218 A1 | 5/2007 | Yodfat et al. | |
| 2007/0124002 A1 | 5/2007 | Estes et al. | |
| 2007/0156092 A1 | 7/2007 | Estes et al. | |
| 2007/0167905 A1 | 7/2007 | Estes et al. | |
| 2007/0167912 A1* | 7/2007 | Causey et al. | 604/131 |
| 2008/0009824 A1 | 1/2008 | Moberg et al. | |
| 2008/0208627 A1 | 8/2008 | Skyggebjerg | |
| 2010/0325864 A1* | 12/2010 | Briones et al. | 29/428 |
| 2012/0330270 A1* | 12/2012 | Colton | 604/500 |

FOREIGN PATENT DOCUMENTS

| | | |
|---|---|---|
| DE | 102 36 669 | 2/2004 |
| DK | PA 2004/01893 | 12/2004 |
| EP | 0 062 974 | 10/1982 |
| EP | 0 275 213 | 7/1988 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| JP | A 9-504974 | 5/1997 |
| JP | 2000-513974 | 10/2000 |
| JP | 2002-507459 | 3/2002 |
| JP | A 2002-523149 | 7/2002 |
| WO | WO 90/15928 | 12/1990 |
| WO | WO 97/21457 | 6/1997 |
| WO | WO 98/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/54753 | 8/2001 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/068015 | 9/2002 |
| WO | WO 02/084336 | 10/2002 |
| WO | WO 02/100469 | 12/2002 |
| WO | WO 03/026726 | 4/2003 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |
| WO | WO 2007/141786 | 12/2007 |

OTHER PUBLICATIONS

Collins and Lee, "Microfluidic flow transducer based on the measurement of electrical admittance," *Lab Chip*, 2004 4 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

OmniPod Insulin Management System-Investor Relations—Press Release, Feb. 1, 2005, http://investors.insulet.com/phoenix/zhtml?c=209336&p=irol-newsArticle&ID=988708&highlight= 1 page.

OmniPod Quick Start Guide, 2007, 2 pages.

Patent Abstracts of Japan, vol. 1999, No. 04, and JP 11 010036, Apr. 30, 1999 and Jan. 19, 1999, Toray Ind. Inc.

The Medtronic Diabetes Connection, 2006, 6 pages.

Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

* cited by examiner

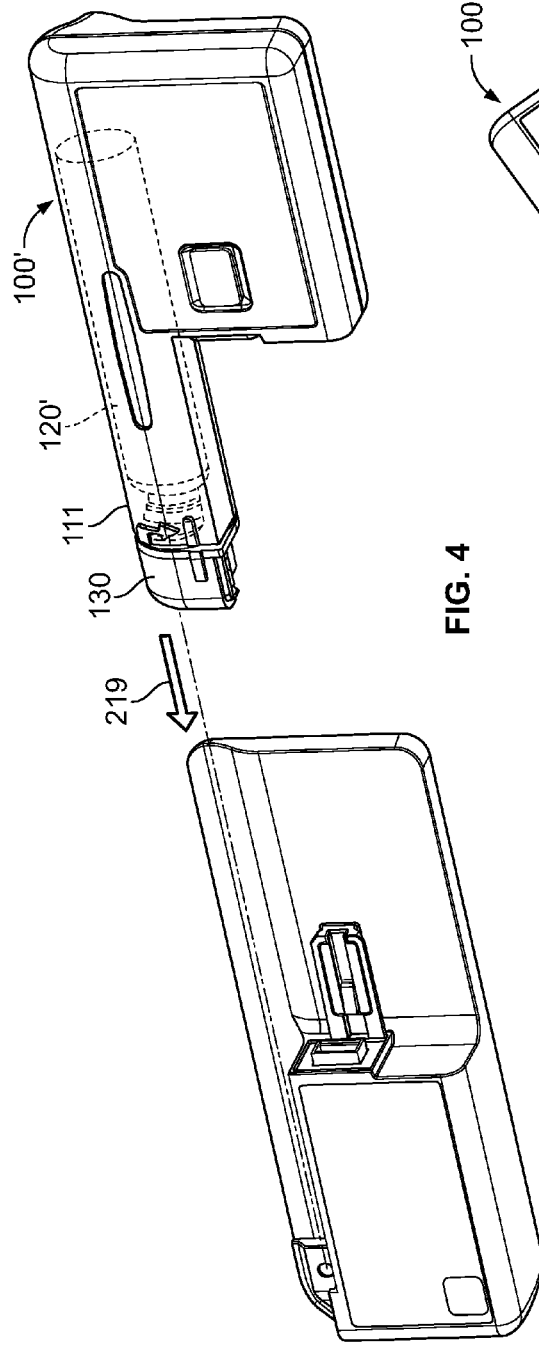
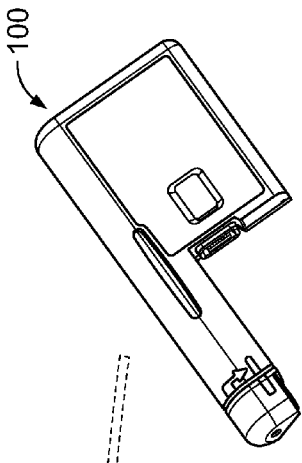
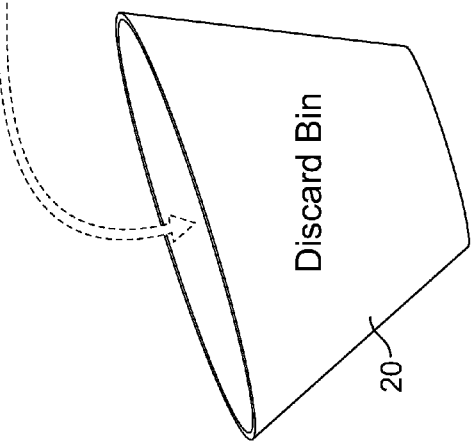
FIG. 4
FIG. 5

INFUSION PUMP SYSTEM AND METHOD

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

In some circumstances, the air pressure external to an infusion pump can be different from the air pressure inside the pump housing. This situation may arise, for example, when a user of an infusion pump travels in an airplane or travels to a location with a different ambient air pressure. In such circumstances, the pressure differential between the interior of the infusion pump and the exterior of the infusion pump can cause unintended dispensation of the medicine from the pump body.

SUMMARY

Some embodiments of an infusion pump system may be configured to provide air pressure equilibrium between the ambient air pressure external to the infusion pump system and the internal air pressure inside the infusion pump system. In particular embodiments, the infusion pump system can be equipped with an air-transmissible, water-resistant seal along an interface between a pump body and a cap device configured to attach to the pump body. In such circumstances, the air-transmissible gasket can protect the internal components housed inside the pump body from water migration or other contamination while also providing an air-transmissible path for air pressure equalization. Also, in some embodiments in which the cap device and pump body are disposable, single-use components that retain a prefilled medicine cartridge therein, the air-transmissible gasket may also be a single-use component, thereby providing the user with a new gasket and seal interface each time a new prefilled medicine cartridge is used.

In particular embodiments, a portable infusion pump system may include a portable housing defining an opening to receive a medicine. The infusion pump system may optionally include a pump drive system arranged in the portable housing and configured to dispense medicine from the portable housing when the medicine is received in the space. Further, the infusion pump system may optionally include a cap device configured to engage with the portable housing to enclose the medicine in the portable housing when the medicine is received in the space. The infusion pump system may also include an air-transmissible gasket positioned at an interface between the portable housing and the cap device. The air-transmissible gasket may include a gasket aperture generally aligned with the opening of the portable housing when the cap device engages with the portable housing. The air-transmissible gasket may also be air-transmissible so that air is passable through the interface between the portable housing and the cap device while the gasket resists migration of liquids into the portable housing.

Other embodiments include a portable infusion pump system that may include a pump device. The pump device may include a pump housing that defines a space to receive a medicine. The pump device may optionally include a drive system positioned in the pump housing to dispense the medicine from the pump device when the medicine is received in the space of the pump housing. Further, the pump device may optionally include a cap device configured to directly attach with the pump housing to enclose the medicine in the pump housing when the medicine is received in the space of the pump housing. The pump device may also include a gasket assembly positioned at an interface between the pump housing and the cap device when the cap device engages with the portable housing. The gasket assembly may be configured to permit the passage of air into and out of the pump housing while resisting the passage of liquids into the pump housing. The gasket assembly may include a hydrophobic member and an elastomeric member, wherein a first major surface of the hydrophobic member is entirely abutted by the elastomeric member. The infusion pump system may also optionally include a controller device that may be removably attachable to the pump housing so as to electrically connect with the pump device. The controller device may house control circuitry, and may be configured to communicate with the drive system positioned in the pump housing to control dispensation of the medicine from the pump device.

Some embodiments include a method of equalizing an air pressure in a space defined by a pump housing of an infusion pump system with an ambient air pressure. The method may include receiving a cap device into attachment with an infusion pump housing so that an air-transmissible gasket is positioned proximate to a cavity opening defined by the infusion pump housing. The method may optionally include maintaining the air-transmissible gasket in a position at an interface between the cap device and a rim of cavity opening of the pump housing. The air-transmissible gasket can be configured to permit passage of air into and out of an interior space defined by the pump housing, while resisting migration of liquid into the interior space defined by the pump housing.

Some or all of the embodiments described herein may provide one or more of the following advantages. First, some embodiments of the infusion pump system may be configured to equalize the air pressure inside the pump device with the air pressure in the region proximately external to the pump device. Second, certain embodiments of an infusion pump system may reduce the likelihood of inadvertent dispensation of medicine caused by a difference in air pressures between an interior space of the pump device and the ambient air pressure. Third, some embodiments of the infusion pump system may provide an air-transmissible and water-resistant seal along an interface between a pump body and a cap device configured to attach to the pump body. In such circumstances, the air-transmissible and water-resistant seal may have a central aperture aligned with a cavity opening of the pump device, thereby facilitating a secure seating from the air-transmissible and water-resistant seal along the cap device (prior to attachment with the pump device). Fourth, the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

Like reference symbols in the various drawings indicate like elements.

DETAILED DESCRIPTION OF ILLUSTRATIVE EMBODIMENTS

Figure 1:
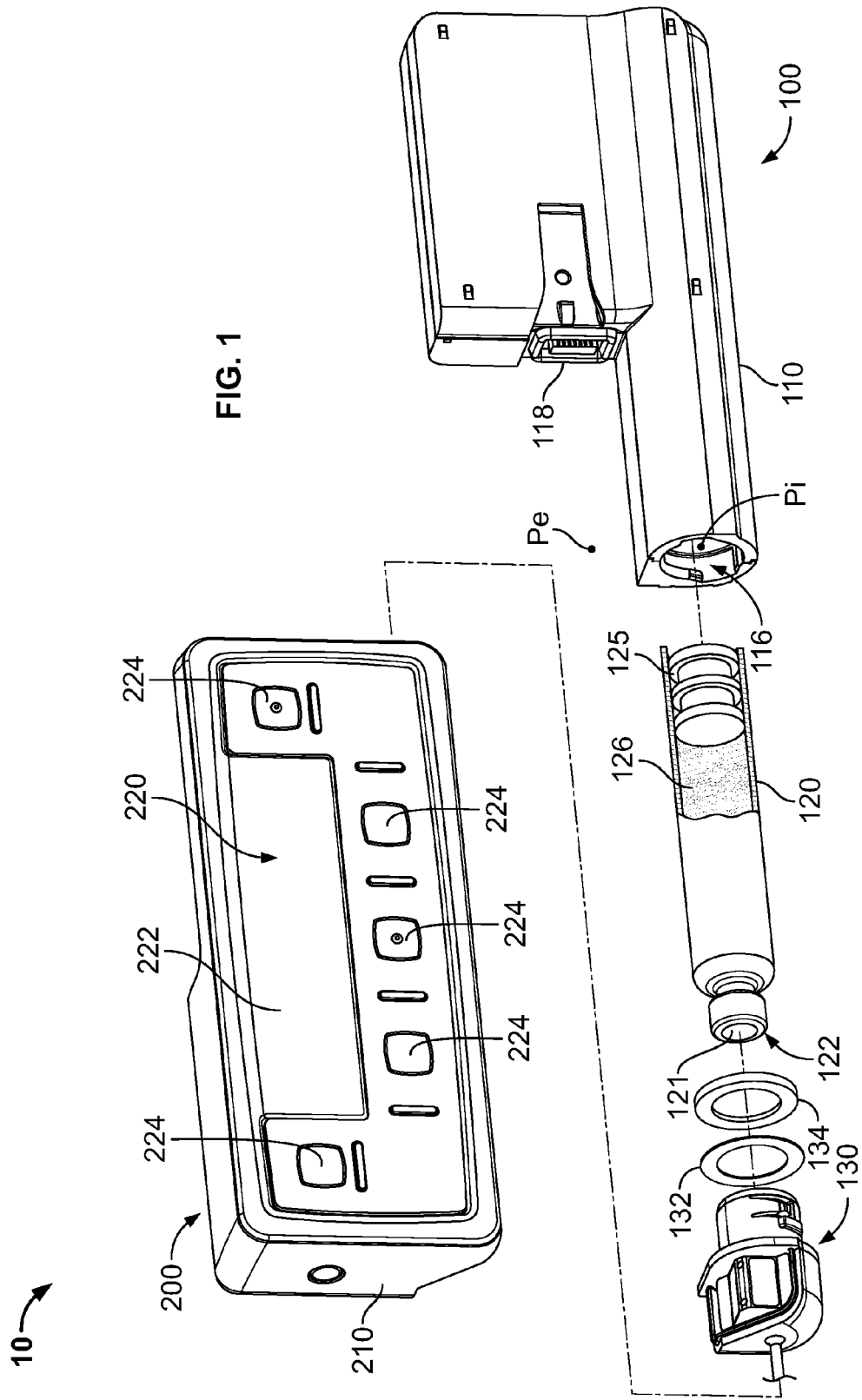
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system that advances a plunger 125 in the fluid cartridge 120 so as to dispense fluid therefrom. As described in more detail below in connection with FIGS. 7-10, some embodiments of the pump device 100 can be advantageously equipped with a water-resistant, air-venting gasket assembly such as an air-transmissible gasket 132 in combination with a ring seal 134. The air-transmissible gasket 132 can facilitate equalization of air pressure between a proximal region external to the pump $P_e$ and a region internal to the pump $P_i$. The air-transmissible gasket 132 and ring seal 134 can also comprise materials that provide a water-resistant seal. This type of water-resistant, air-venting gasket assembly can prevent changes in ambient air pressure from adversely affecting the dosage amount delivered by the infusion pump system 10, while maintaining resistance to water migration to the pump device 100. Moreover, the position of the air-transmissible gasket 132 (e.g., on the cap device 130 and proximate to the opening of the cavity 116) can provide improve functionality while reducing the complexity of manufacturing the pump device 100.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3). Moreover, at least one of the pump device 100 or the controller device 200 can include a release member that facilitates an easy-to-use detachment and replacement process.

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. In another example, the cap device 130 can be configured to irreversible attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 6) of the controller device 200 and from the power source 310 (refer to FIG. 7) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

Figure 2:
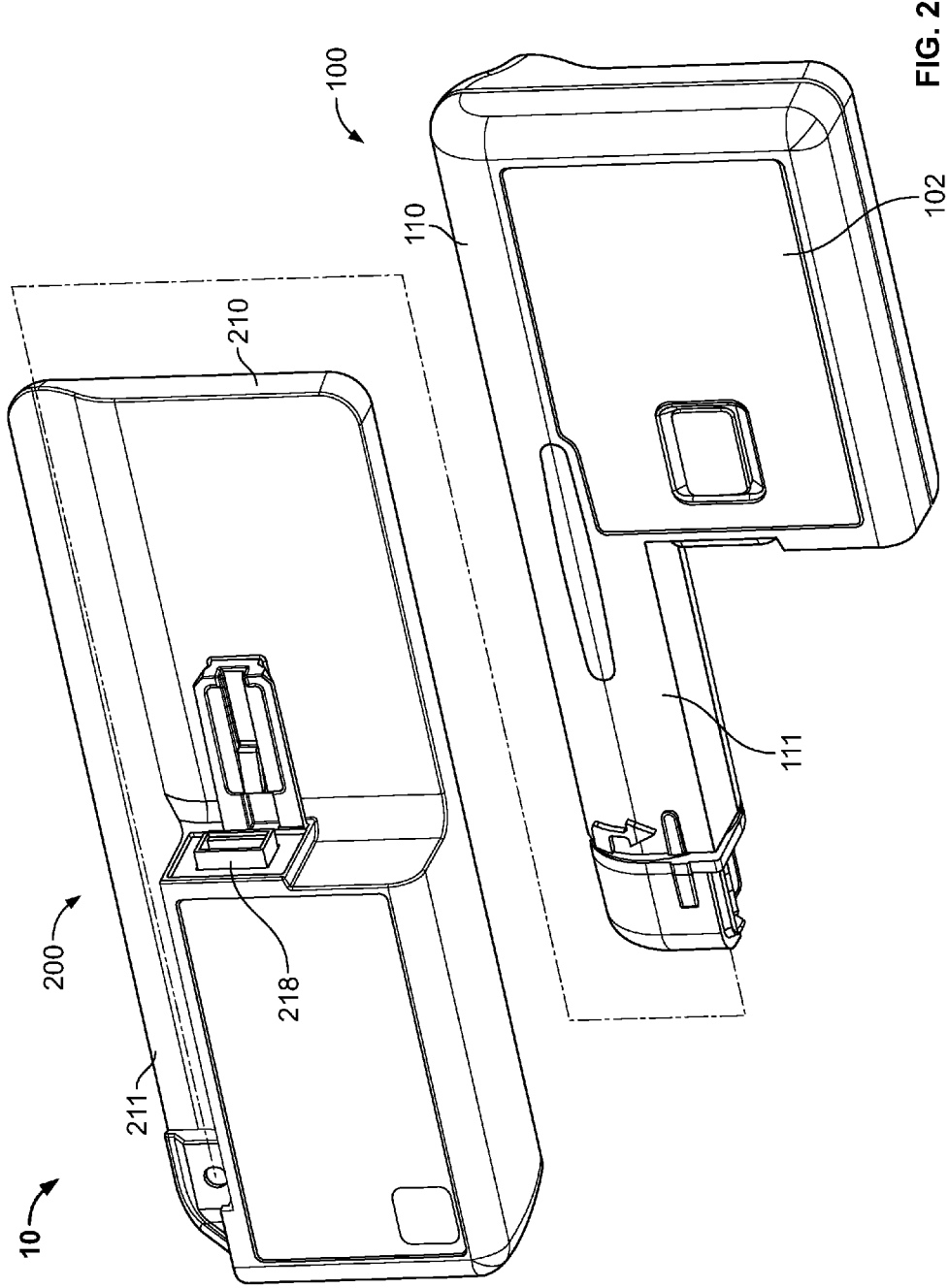
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 3:
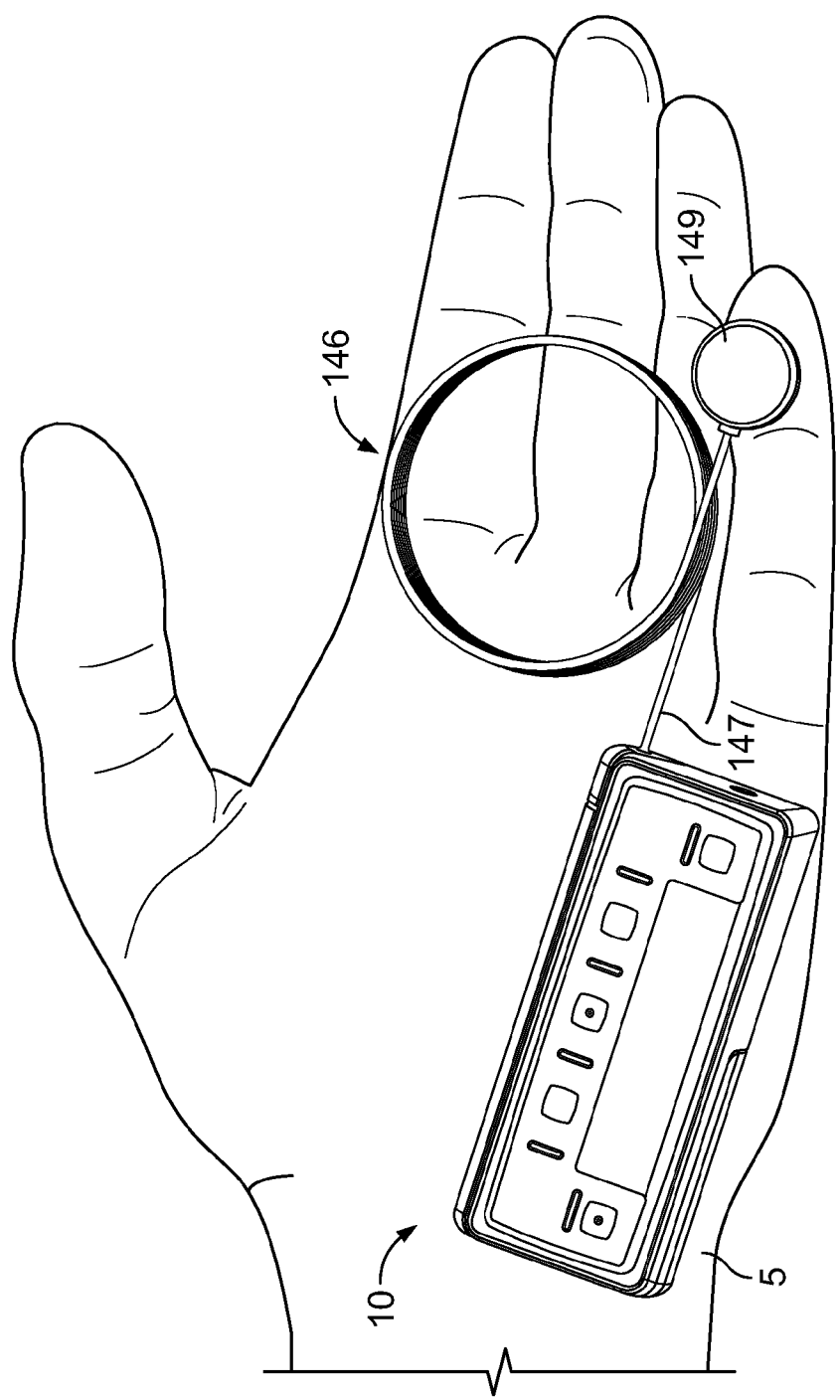
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 6:
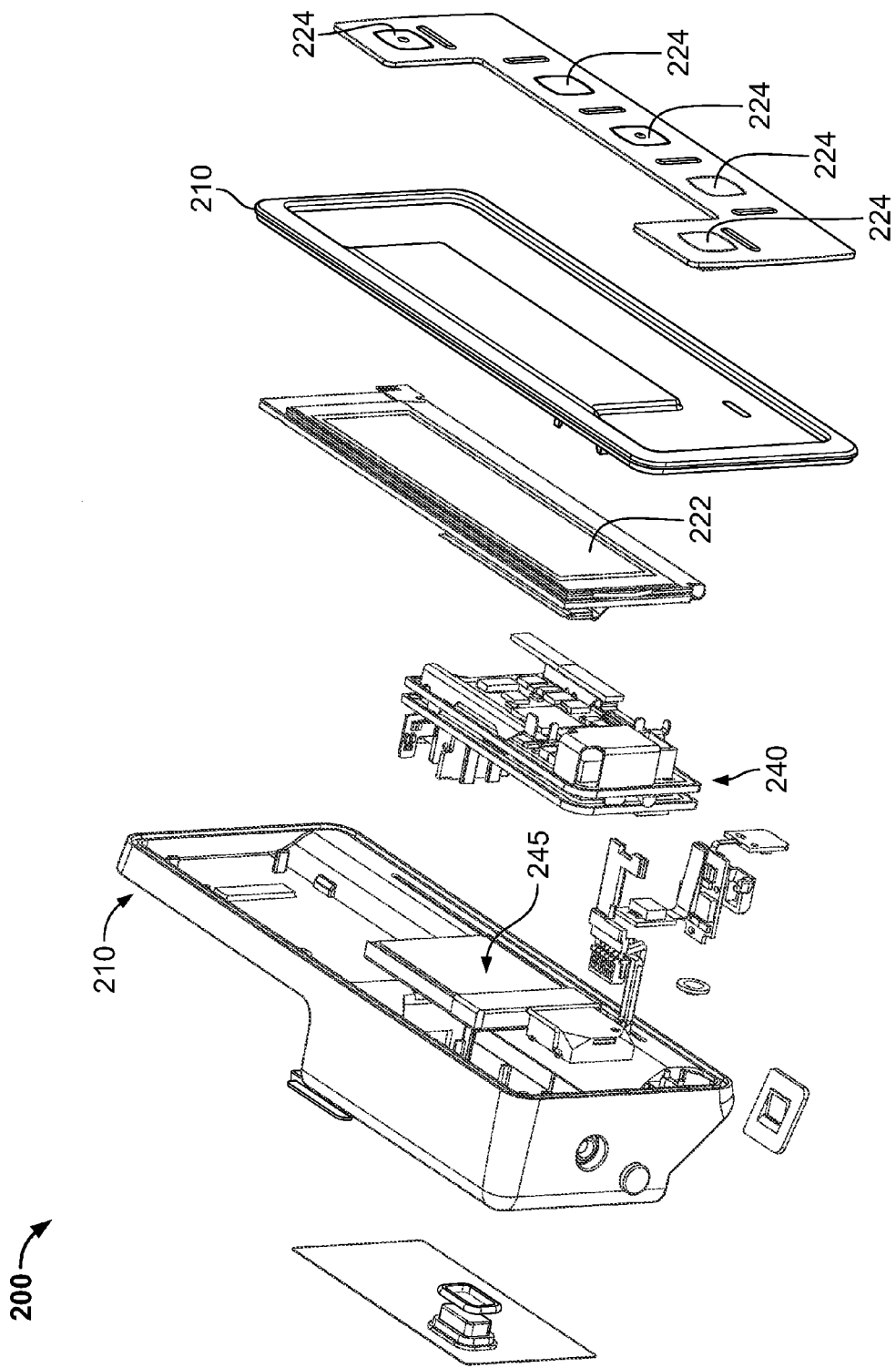
FIG. 6 is an exploded perspective view of a controller device for an infusion pump system, in accordance with some embodiments.

Referring now to FIG. 6, the controller device 200 (shown in an exploded view) houses a number of components that can be reused with a series of successive pump devices 100. In particular, the controller device 200 can include controller circuitry 240 and a rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or to components of the pump device 100. Controller circuitry 240 may be configured to communicate control or power signals to the drive system of the pump device 100, or to receive power or feedback signals from the pump device 100.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in one or more memory devices arranged in the controller circuitry 240.

In some optional embodiments, the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry or to download data from the controller circuitry. For example, historical data of medicine delivery can be downloaded from the controller circuitry 240 (via the cable connector) to a computer system of a physician or a user for purposes of analysis and program adjustments. Optionally, the data cable can also provide recharging power.

Figure 7:
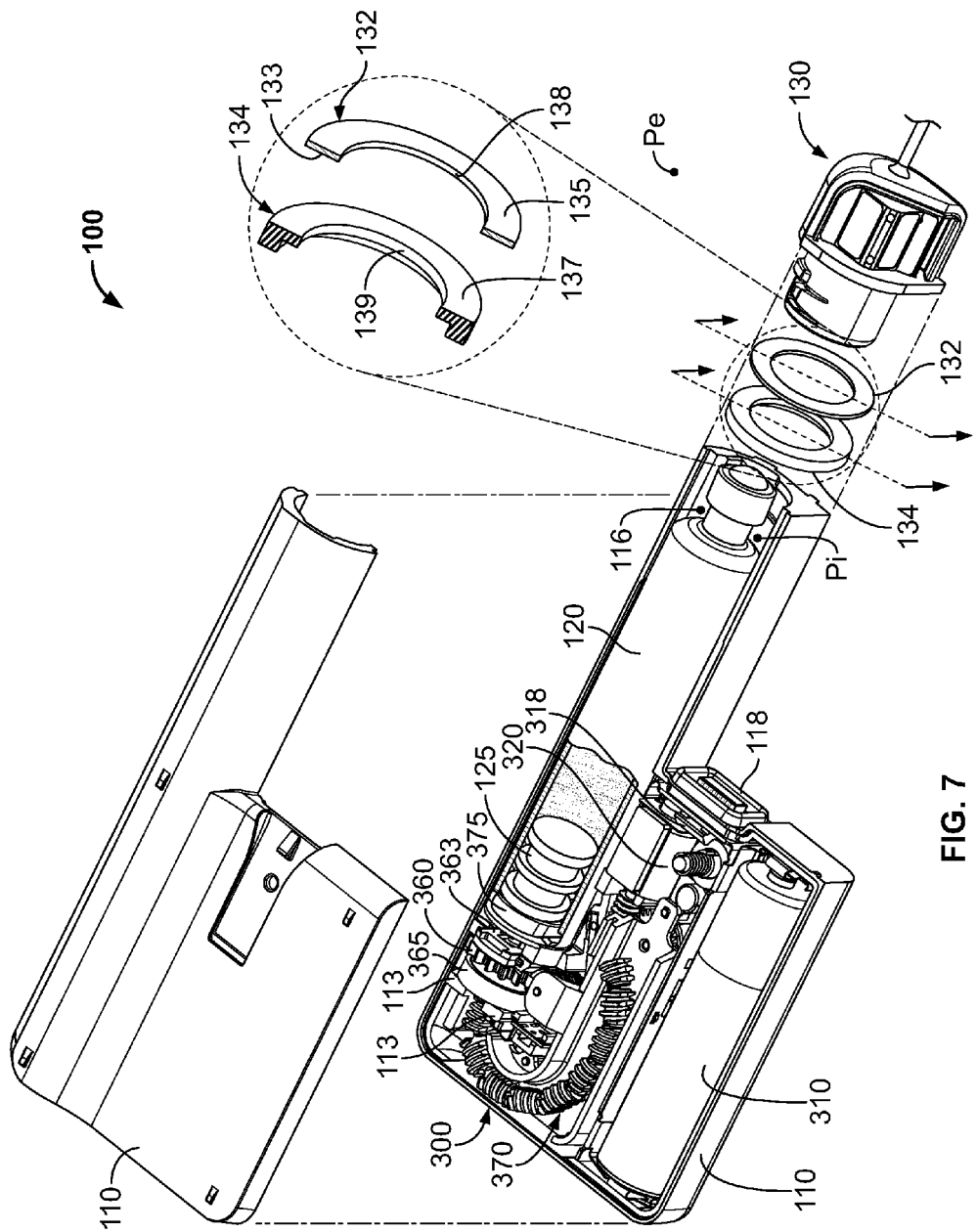
FIG. 7 is an exploded perspective view of a pump device for an infusion pump system, in accordance with some embodiments.

Referring now to FIG. 7, the pump device 100 can include a drive system 300 that is controlled by the controller device 200. As described in more detail below, the drive system 300 can incrementally dispense fluid in a controlled manner from cartridge 120 inserted into the pump device 100. Also, the pump device 100 may include a connector circuit 318 to facilitate the transfer of signals to and from the electrical connector 118. In some implementations, the connector circuit 318 in the pump device 100 may include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connector circuit 318 can operate as a passageway to transmit electrical control signals from the controller circuitry 240 of the controller device 200 to the drive system 300. The connector circuit 318 can also operate as a passageway for the electrical power from a power source 310 housed in the pump device 300 to pass to the controller device 200 for recharging of the rechargeable battery 245. Furthermore, the connector circuit 318 can operate as a passageway for feedback signals from the drive system 300 to the controller circuitry 240 of the controller device 200.

In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 7, in some embodiments, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 375. In this embodiment, the reversible motor 320 drives a gear system (not shown in FIG. 7) to cause the rotation of the drive wheel 360 that is coupled with the bearing 365. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 7, the drive wheel 360 is the driver while the flexible piston rod 370 is the driven member. As further described below, the rotation of the drive wheel 360 can drive the flexible piston rod 370 forward in a linear longitudinal direction. The flexible piston rod 370 can, in turn, contact and drive forward a plunger 125 in the fluid cartridge 120 so as to dispense fluid therefrom.

As shown in FIG. 7, some embodiments of the pump device 100 can be equipped with the water-resistant, air-venting gasket assembly including the air-transmissible gasket 132 in combination with the ring seal 134. In the depicted embodiment, the water-resistant, air-venting gasket assembly is secured to the cap device 130 and positioned to provide a water resistant seal along the interface between the cap device 130 and the pump housing 110. As previously described, the pump housing 110 defines the cavity 116 configured to slidably receive the fluid cartridge 120. Accordingly, the air-transmissible gasket 132 and ring seal 134 are arranged so that interior air pressure $P_i$ in the cavity 116 can reach approximate equilibrium with the exterior air pressure $P_e$ even though the seal resists water migration into the cavity 116.

In this embodiment, the air-transmissible gasket 132 and the ring seal 134 can both have a generally circular shape with a central aperture therethrough. For example, as shown in FIG. 7 (and also shown later in FIG. 9), the air-transmissible gasket 132 may comprise a generally flat disc-shaped structure that is configured to abut with the ring seal. The air-transmissible gasket 132 can comprise a first major surface 133 that is generally planar, a second, opposite major surface 135 that is generally planner, and an inner rim 138 that defines a central aperture therethrough. The first major surface 133 of the air-transmissible gasket 132 can be sized so that it entirely abuts with a first major surface 137 of the ring seal 134. Even though the ring seal 134 is not necessarily air-transmissible and thereby may prevent air transmission in a path exiting from or passing into the first major surface 133 of the air-transmissible gasket 132, the air-transmissible gasket 132 may provide air transmission in a path exiting from or passing into the surface of the inner rim 138 of the air-transmissible gasket 132 (as described below in connection with FIG. 9). In this embodiment, the ring seal 134 may comprise a generally "L-shaped" cross-section so that an inner rim 139 of the ring seal 134 is configured to be retained in an annular seat 136 (FIG. 9) of the cap device 130, as described in more detail below. Also, in this embodiment, the inner rim 138 of the air-transmissible gasket 132 and the inner rim 139 of the ring seal 134 can be substantially similar in size, with both of them being generally axially aligned and being generally aligned with the cavity 116 of the pump housing (when the cap device 130 is attached to the pump housing 110).

Still referring to FIG. 7 such a water-resistant seal between the cap device 130 and the pump housing 110 provides a functional benefit in that it protects sensitive internal components in the pump device 100 from damage by water migration in the event that the user encounters water (e.g. rain, incidental splashing, and the like). To accomplish this, air-transmissible gasket 132 and ring seal 134 can be constructed from materials that are generally resistant to liquid penetration. Further, at least one of the air-transmissible gasket 132 and ring seal 134 can preferably be sufficiently compliant to enable a tight and conformant physical seal between the cap device 130 and the pump housing 110. For example, the ring seal 134 can comprise a pliable elastomeric material such as silicone, nitrile rubber, natural rubber, polyurethane, and neoprene. Those materials can enable ring seal 134 to be compliant, pliable, and to provide a water-resistant seal.

In particular embodiments, the air-transmissible gasket 132 can comprise a material that is different from the elastomeric material of the ring seal 134. For example, the air-transmissible gasket 132 can be configured to allow the passage of air between the internal and external regions of the pump device 100 while also resisting water migration into the pump cavity 116. As such, the air-transmissible gasket 132 may comprise a hydrophobic material (e.g., a material that permits air to pass therethrough while resisting the passage of water or other liquids from doing so). For example, the air-transmissible gasket 132 may comprise a hydrophobic material such as GORE-TEX® (W.L. Gore & Associates, Inc. of Newark, Del.), POREX® (Porex Corporation of Fairburn, Ga.), PTFE, or HDPE.

This air-venting capability of the air-transmissible gasket 132 can serve to prevent changes in ambient air pressure from potentially adversely affecting the dosage delivered by the infusion pump system 10. For example, a user of the infusion pump system 10 may take an airplane flight during which the air pressure external to the pump system $P_e$ will be reduced as compared to the air pressure on land. If the air pressure within the pump housing $P_i$ is not allowed to vent, it will remain higher than the external pressure $P_e$. That pressure differential could result in a pressure being exerted on the plunger 125, which in turn could result in an inadvertent dispensation of fluid from the fluid cartridge 120. Conversely, if the air pressure external $P_e$ to the pump device 100 is higher than inside the pump housing $P_i$, the plunger may be subject to a suction force that may cause an inadvertent retraction of medicine from infusion set tubing. Consequently, the infusion pump system 10 can benefit from a system which permits an equalization of an air pressure differential between the regions external to the pump $P_e$ and internal to the pump $P_i$. As described in more detail below, the air-transmissible gasket 132 can function to provide such equalization of air pressures.

Figure 8:
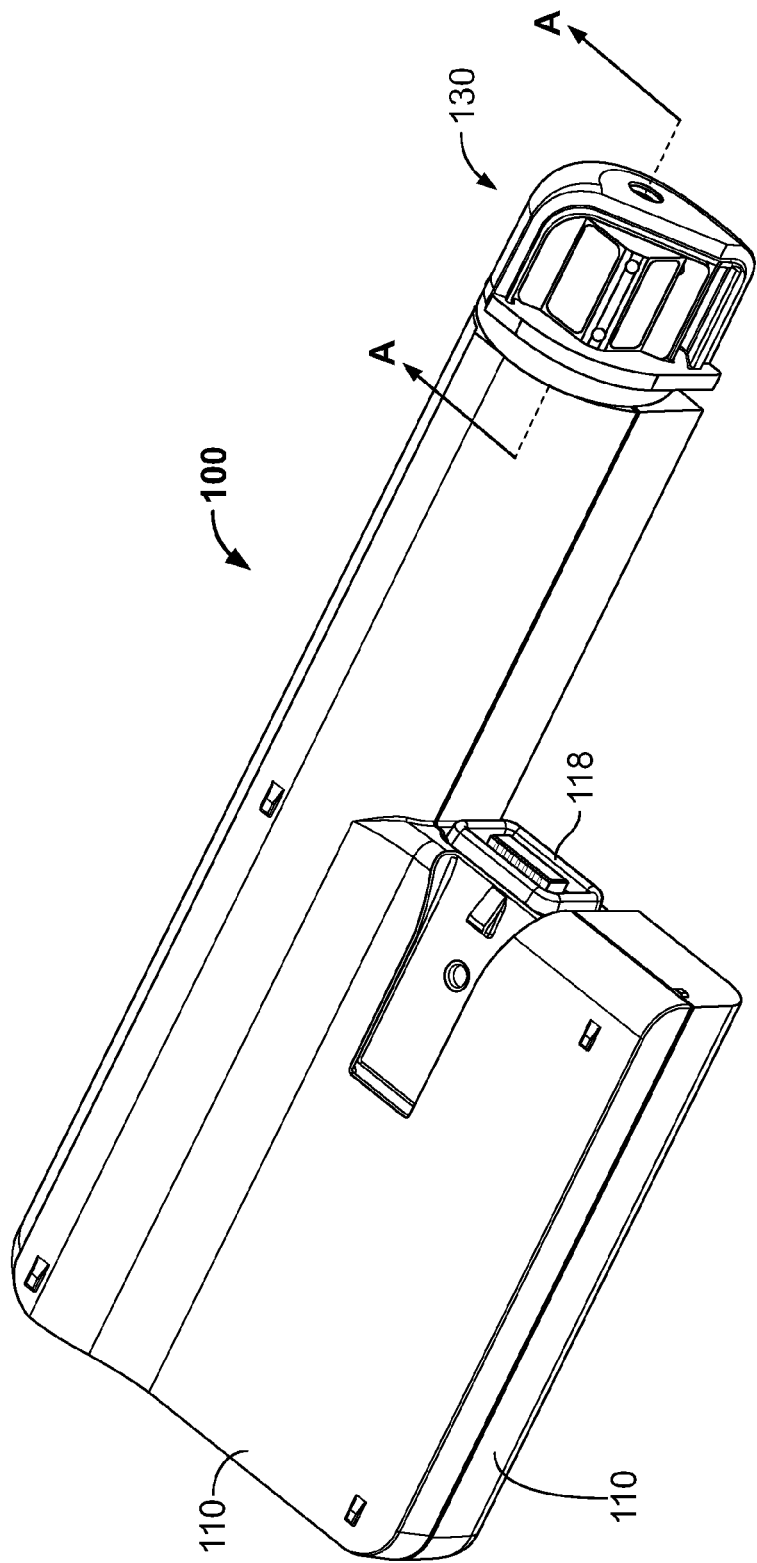
FIG. 8 is a perspective view of a pump device assembled with a cap device including an air-transmissible gasket of the infusion pump system of FIG. 1.
Figure 9:
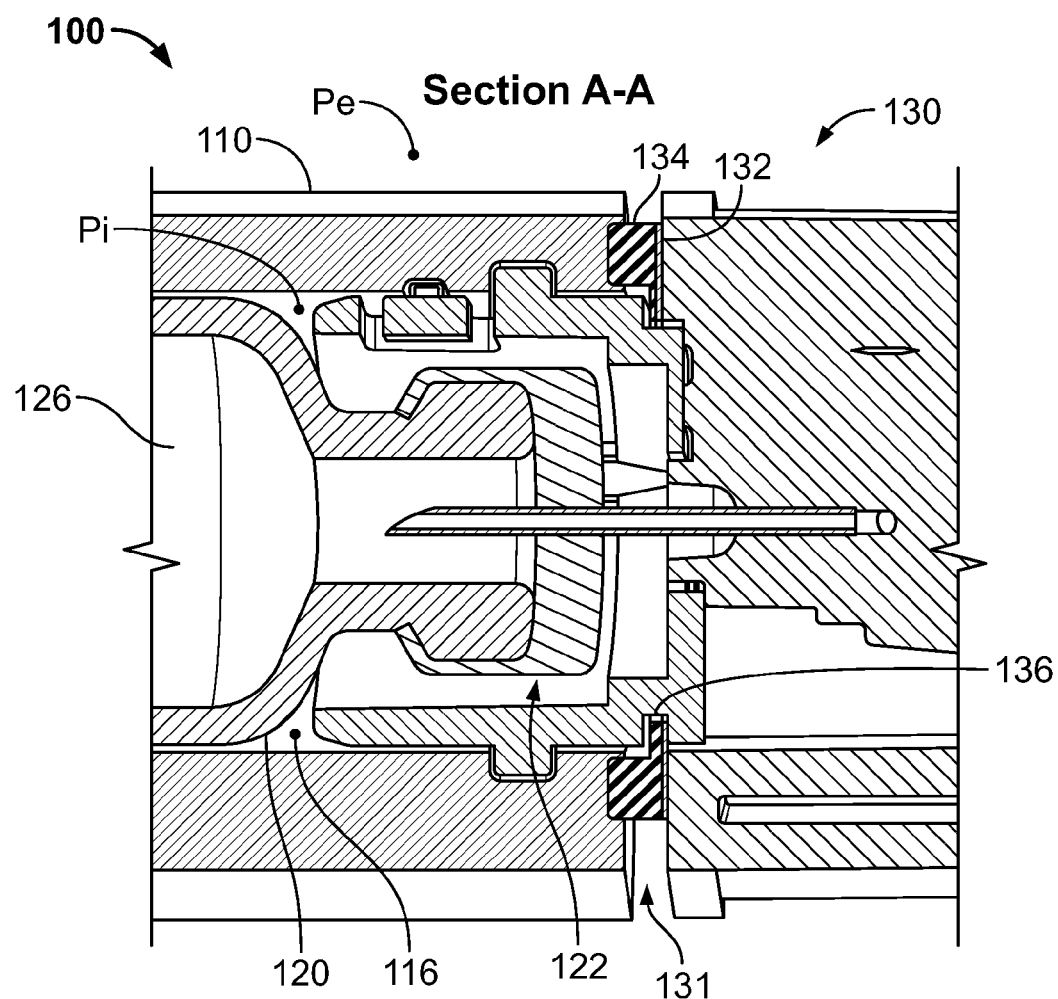
FIG. 9 is a cross-sectional view of a pump device assembled with a cap device including an air-transmissible gasket of the infusion pump system of FIGS. 1 and 8.

Referring now to FIGS. 8-9, the water-resistant, air-venting gasket assembly can be provided by air-transmissible gasket 132 and ring seal 134 located between the cap device 130 and the pump housing 110, with the gasket 132 and seal 134 being compressed between the pump housing 116 and the cap device 130. In this embodiment, the air-transmissible gasket 132 and ring seal 134 can be physically seated and retained in a groove 136 (FIG. 9) located on the outer barrel of cap device 130. With the air-transmissible gasket 132 and ring seal 134 seated in groove 136, the water-resistant, air-venting gasket assembly can be retained by the cap device 130 even before it is attached to the pump housing 110. Furthermore, the seating of the air-transmissible gasket 132 and ring seal 134 in the groove 136 facilitates proper positioning and functionality of the water-resistant, air-venting seal during attachment of the cap device 130 with the pump housing 110, which can thereafter be maintained during the life of the pump device 100 (e.g., until exhaustion of the medicine cartridge 120 or other such events).

As shown, the air-transmissible gasket 132 and ring seal 134 can be maintained in physical contact with each other. In this example configuration, the first major surface 133 of air-transmissible gasket 132 is in contact with first major surface 137 of the ring seal 134 (as previously described in connection with FIG. 7). As such, in some cases, the path for air transmission through air-transmissible gasket 132 can be through the smaller surface at the inner rim 138 (FIG. 7) rather than through the first major surface 137 (which abuts the elastomeric material of the ring seal 134). Such an air path through air-transmissible gasket 132 can enable an air flow for the equalization of an air pressure differential between the pressure in a region external to the pump $P_e$ and internal to the pump $P_i$. For example, the air path can pass from the interior of the cavity 116, along the annular surface of the seat 136, through the inner rim 138 of the gasket 132, through the outer periphery of the gasket 132, and out through a gap 131 between the pump housing 110 and an opposing face of the cap device 130. (It should be understood that the gap 131 can be smaller than what is depicted in FIG. 9.) The ring seal 134, as shown, can be in contact with the air-transmissible gasket 132 on one side and the rim of the cavity 116 of the housing structure 110 on the other side. Thus, when the cap device 130 is threaded into engagement with the pump housing 110, the ring seal 134 is subject to axial compression between the pump housing 110 and the cap device 130. This example configuration of air-transmissible gasket 132 and ring seal 134 can provide the aforementioned water-resistant, air-venting capabilities during use of the pump device 100.

Figure 10:
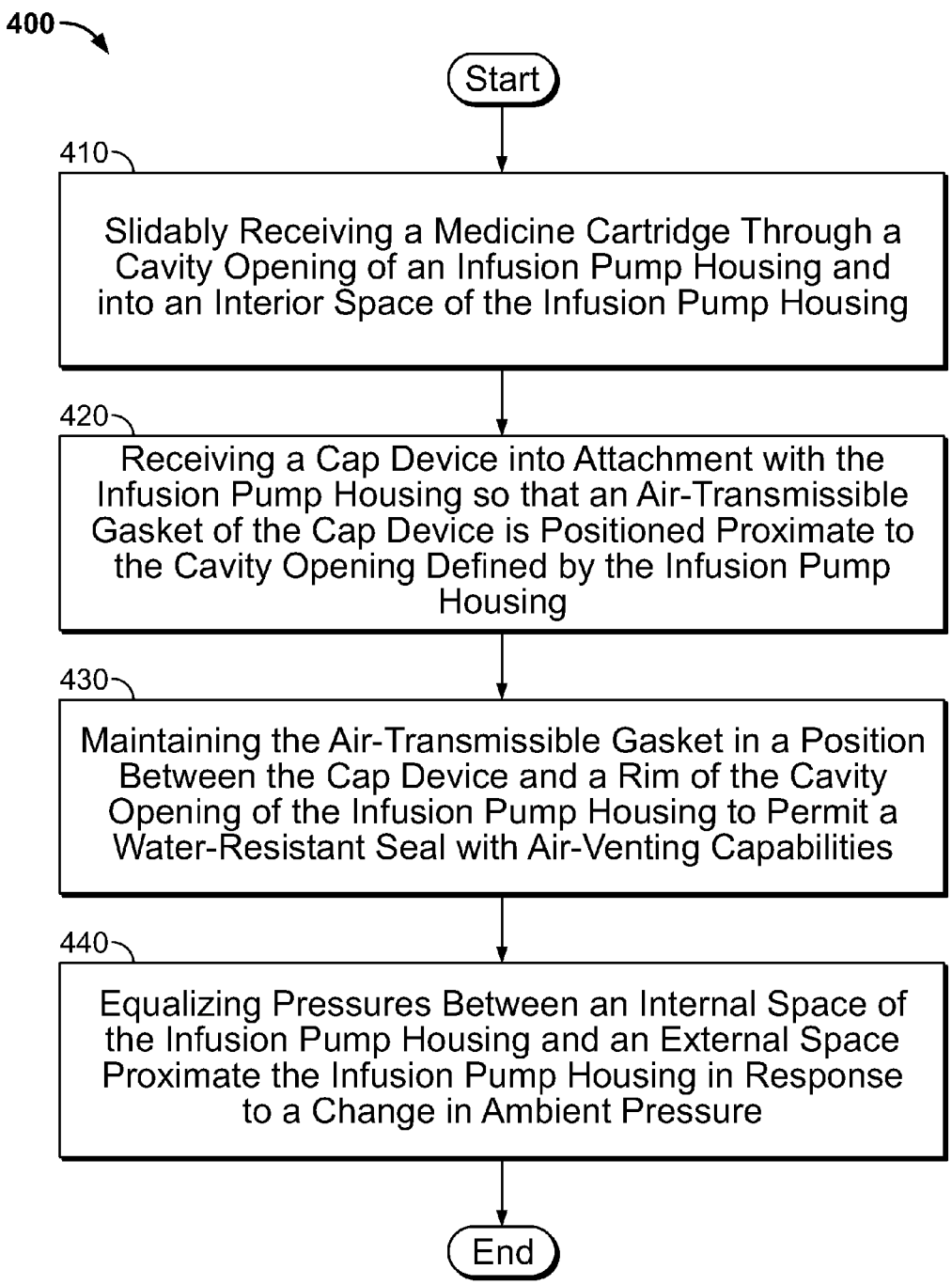
FIG. 10 is a flow chart of a process for using an infusion pump system equipped with an air-transmissible gasket.

FIG. 10 illustrates a process 400 by which a medicine infusion pump device can provide pressure equalization between an interior pressure (e.g., inside the pump device) and the ambient pressure. This process 400 can be implemented, for example, by an infusion pump system like the pump system 10 described in connection with FIGS. 1-9. In those embodiments, the pump system 10 can realize a state of air pressure equilibrium between a space that is external to the pump system 10 and a space that is internal to the pump system 10 even when the pump system 10 is exposed to a gradient in ambient pressure.

Optionally, the infusion pump pressure equilibrium process 400 includes operation 410 of slidably receiving a medicine cartridge through a cavity opening of an infusion pump housing and into an interior space of the infusion pump housing. For example, in some implementations involving the pump system 10 (FIGS. 1-9), the medicine cartridge 120 is slidably received in the cavity 116 of the pump housing 110.

The process 400 may also include the operation 420 of receiving a cap device into attachment with the infusion pump housing so that an air-transmissible gasket of the cap device is positioned proximate to the cavity opening defined by the infusion pump housing. For example, in some implementations involving the pump system 10 (FIGS. 1-9), the cap device 130 is received into attachment with the pump housing 110 so that the air-transmissible gasket 132 is proximate to the opening of the cavity 116, which (as previously described) permits air transmission between the interior and exterior regions of the pump system 10 in the event of an air pressure differential between those two regions.

In operation 430, the air-transmissible gasket is maintained in a position between the cap device and a rim of the cavity opening of the infusion pump housing. Such positioning of the air-transmissible gasket is configured to permit a water-resistant seal with air-venting capabilities. For example, in some implementations involving the pump system 10 (FIGS. 1-9), the air-transmissible gasket 132 is part of the water-resistant, air-venting gasket assembly arranged along an interface of the cap device 130 and the pump housing 110. As described in detail above, the air-transmissible gasket 132 in combination with the ring seal 134 can provide the air-venting capabilities while also protecting against water migration into the interior of the pump device 100.

The process 400 may also include the operation 440 of equalizing pressures between the interior space of the infusion pump housing and an external space proximate to the infusion pump housing in response to a change in ambient pressure. For example, in some implementations involving the pump system 10 (FIGS. 1-9), the infusion pump system 10 may be exposed to an ambient pressure change. In response, the pump system 10 can be configured to equalize the internal air pressure $P_i$ in the cavity 116 with the ambient air pressure $P_e$ via the air-transmissible gasket 132. For example, if a user takes the pump system 10 onto an airplane the air pressure in the cabin of the airplane while in-flight will be lower than the air pressure on land prior to take-off. Using the infusion pump pressure equilibrium process 400, the higher air pressure in the interior of pump system will be vented through an air-transmissible gasket so that the pump system's interior air pressure will be reduced to equal the air pressure in the cabin of the airplane. In this manner, the potentially adverse effects of a pressure gradient between the interior and exterior of an infusion pump system 10 can be mitigated.

A number of embodiments of the invention have been described. Nevertheless, it will be understood that various modifications may be made without departing from the spirit and scope of the invention. Accordingly, other embodiments are within the scope of the following claims.

What is claimed is:

1. A portable infusion pump system, comprising:
   a portable housing defining an opening to receive a medicine;
   a pump drive system arranged in the portable housing and configured to dispense medicine from the portable housing when the medicine is received in the space;
   a cap device configured to engage with the portable housing to enclose the medicine in the portable housing when the medicine is received in the space; and
   an air-transmissible gasket positioned at an interface between the portable housing and the cap device and comprising a gasket aperture generally aligned with the opening when the cap device engages with the portable housing, wherein the gasket is air-transmissible so that air is passable through the interface between the portable housing and the cap device while the gasket resists migration of liquids into the portable housing.

2. The portable infusion pump system of claim 1, wherein the air-transmissible gasket is seated in an annular groove defined by the cap device.

3. The portable infusion pump system of claim 1, wherein the air-transmissible gasket comprises a hydrophobic material.

4. The portable infusion pump system of claim 1, further comprising a ring seal abutted with the air-transmissible gasket, wherein the ring seal comprises an elastomeric material.

5. The portable infusion pump system of claim 4, wherein the air-transmissible gasket comprises a first major surface, a second major surface, and an inner rim that defines the gasket aperture, and wherein the entire first major surface is positioned in abutment with the elastomeric material of the ring seal.

6. The portable infusion pump system of claim 5, wherein the ring seal comprises a generally L-shaped cross-section that defines an inner rim of the elastomeric member, the inner rim of the elastomeric member being seated within an annular grove defined by the cap device.

7. The portable infusion pump system of claim 6, wherein the inner rim of the ring seal defines a seal aperture, wherein both the gasket aperture of the gasket and the seal aperture of the ring seal are generally axially aligned the opening of the portable housing when the cap device engages with the portable housing.

8. The portable infusion pump system of claim 7, wherein the inner rim of the gasket provides an air path for passage of air into and out of the portable housing.

9. The portable infusion pump system of claim 1, further comprising control circuitry that electrically communicates with the pump drive system to control dispensation of the medicine from the portable housing when the medicine is received in the space.

10. The portable medical infusion pump system of claim 9, wherein the control circuitry is housed in a removable controller device that is removably attachable to the portable housing.

11. A portable infusion pump system, comprising:
 a pump device including a pump housing that defines a space to receive a medicine, a drive system positioned in the pump housing to dispense the medicine from the pump device when the medicine is received in the space of the pump housing, a cap device configured to directly attach with the pump housing to enclose the medicine in the pump housing when the medicine is received in the space of the pump housing, and a gasket assembly positioned at an interface between the pump housing and the cap device when the cap device engages with the portable housing, wherein the gasket assembly is configured to permit the passage of air into and out of the pump housing while resisting the passage of liquids into the pump housing, the gasket assembly comprising a hydrophobic member and an elastomeric member, wherein a first major surface of the hydrophobic member is entirely abutted by the elastomeric member; and
 a controller device removably attachable to the pump housing so as to electrically connect with the pump device, wherein the controller device houses control circuitry configured to communicate with the drive system positioned in the pump housing to control dispensation of the medicine from the pump device.

12. The portable infusion pump system of claim 11, wherein the gasket assembly is seated in an annular groove defined by the cap device.

13. The portable infusion pump system of claim 12, wherein the elastomeric member comprises a generally L-shaped cross-section that defines an inner rim of the elastomeric member, the inner rim of the elastomeric member being seated within the annular grove defined by the cap device.

14. The portable infusion pump system of claim 11, wherein the hydrophobic member comprises the first major surface, a second major surface, and an inner rim that defines an aperture through the hydrophobic member, the aperture of the hydrophobic member being generally aligned with an opening defined by the pump housing when the cap device engages with the portable housing.

15. The portable infusion pump system of claim 11, wherein the inner rim of the hydrophobic member provides an air path for the passage of air into and out of the pump housing.

16. A method of equalizing an air pressure in a space defined by a pump housing of an infusion pump system with an ambient air pressure, the method comprising:
 receiving a cap device into attachment with an infusion pump housing so that an air-transmissible gasket is positioned proximate to a cavity opening defined by the infusion pump housing; and
 maintaining the air-transmissible gasket in a position at an interface between the cap device and a rim of cavity opening of the pump housing, wherein the air-transmissible gasket is configured to permit passage of air into and out of an interior space defined by the pump housing while resisting migration of liquid into the interior space defined by the pump housing.

17. The method of claim 16, further comprising, in response to a change in ambient air pressure, equalizing an air pressure in the interior space defined by the pump housing with an air pressure external to the pump housing.

18. The method of claim 16, further comprising slidably receiving a medicine cartridge through the cavity opening of the pump housing and into the interior space defined by the pump housing.

19. The method of claim 16, wherein the cap device comprises a ring seal abutted with the air-transmissible gasket, wherein the ring seal comprises an elastomeric material.

20. The method of claim 19, wherein the air-transmissible gasket comprises a first major surface, a second major surface, and an inner rim that defines a gasket aperture, wherein the gasket aperture is generally aligned with the cavity opening when the cap device attaches with the portable housing, and wherein the entire first major surface is positioned in abutment with the elastomeric material of the ring seal.

* * * * *